Figure 1:
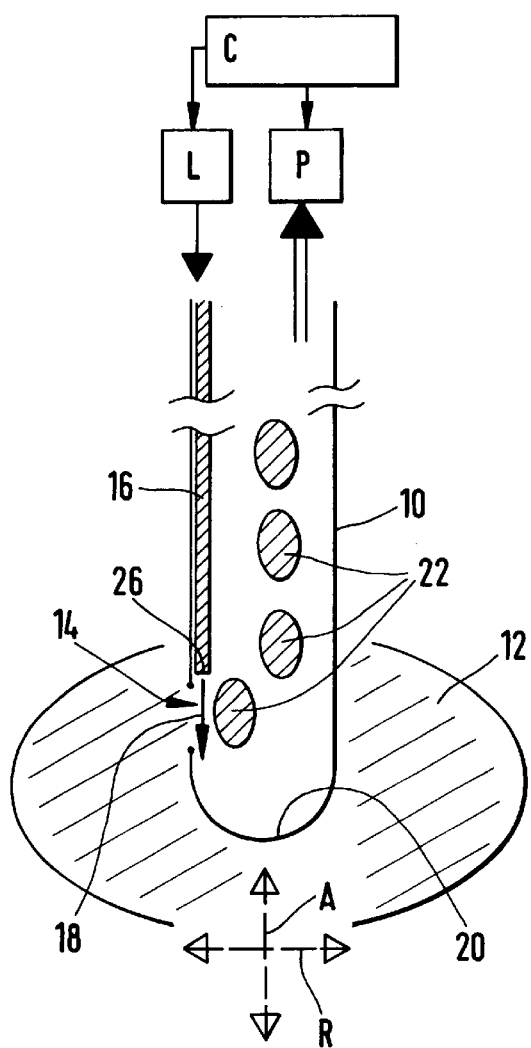

United States Patent
Donitzky et al.

[11] Patent Number: 6,027,493
[45] Date of Patent: Feb. 22, 2000

[54] DEVICE AND METHOD FOR THE REMOVAL OF BODY SUBSTANCES

[75] Inventors: Christof Donitzky, Eckental; Max Reindl, Heroldsberg; Fredy Strohm, Neunkirchen am Brand, all of Germany

[73] Assignee: Wavelight Laser Technologie GmbH, Erlangen, Germany

[21] Appl. No.: 09/057,073

[22] Filed: Apr. 8, 1998

[30] Foreign Application Priority Data

Apr. 8, 1997 [DE] Germany ............ 197 14 475

[51] Int. Cl.$^7$ .............. A61B 17/36; A61B 17/32
[52] U.S. Cl. ............ 606/4; 606/10; 606/11; 606/170; 606/171
[58] Field of Search .................. 606/2, 4, 170, 606/171, 107, 10, 11; 604/118

[56] References Cited

U.S. PATENT DOCUMENTS

| | | |
|---|---|---|
| 4,122,853 | 10/1978 | Smith . |
| 4,650,460 | 3/1987 | Roizenblatt .............. 604/22 |
| 5,020,535 | 6/1991 | Parker et al. ............ 606/174 |
| 5,285,795 | 2/1994 | Ryan et al. ............ 606/170 X |
| 5,487,725 | 1/1996 | Peyman . |
| 5,505,210 | 4/1996 | Clement ............... 606/170 X |
| 5,547,473 | 8/1996 | Peyman . |
| 5,788,667 | 8/1998 | Stoller ............... 606/170 X |

FOREIGN PATENT DOCUMENTS

| | | |
|---|---|---|
| 74 39 950 U1 | 8/1982 | Germany . |
| 38 31 141 A1 | 3/1990 | Germany . |
| 44 07 949 A1 | 9/1995 | Germany . |

OTHER PUBLICATIONS

R. Klöti, "Glaskörperverlust—weniger gefährlich mit dem Mikrostripper", Klin. Mbl. Augenheikunde (1982); 120: 447–450.

Jeffrey W. Berger, Thomas W. Bochow, Jonathan H. Talamo, Donald J. D'Amico, "Measurement and Modeling of Thermal Transients During Er:YAG Laser Irradiation of Vitreous", Lasers in Surgery and Medicine 19: 388–396 (1996).

H. Büttner, R. Machemer, "Erkrankungen am Glaskörper des Auge4s sind heilbar", Umschau, 1974, Bd. 74. Heft 22, S. 716–717.

*Primary Examiner*—Jeffrey A. Smith
*Attorney, Agent, or Firm*—Woodard, Emhardt, Naughton Moriarty & McNett Patent and Trademark Attorneys

[57] ABSTRACT

An appliance for the removal of body substance, in particular an ophthalmological vitrectomy device, uses a mechanical cutting edge or laser radiation (18) for detaching vitreous body material. Detached parts of vitreous body material (22) are suctioned off by an aspiration cannula (10). To avoid traction in the vitreous body material (12), a control system (C) for the time sequence, energy and length of the laser pulses (18) and for the suction pump (P) is provided. The control is effected in such a way that a volume (22) of vitreous body material suctioned through the opening (14) is in each case detached free of traction, by one or more laser pulses, from the remaining vitreous body material (12) located in the eye, before a further volume of vitreous body material is suctioned in. The exit direction of the laser beam pulses (18) from the radiation conductor (16) is transverse to the aspiration direction.

11 Claims, 1 Drawing Sheet

DEVICE AND METHOD FOR THE REMOVAL OF BODY SUBSTANCES

The invention relates to a device for the removal of body substance, having an aspiration cannula.

Such a device is known from DE 38 31 141 A1.

The invention relates in particular to a device of the above-described type for vitrectomy, that is to say for removal of vitreous body material from the eye. The invention is hereinafter explained by way of example, first with reference to vitrectomy.

The term "vitrectomy" is understood by the ophthalmologist (eye specialist) as the removal of vitreous body substance from the eyeball. The spherical human eyeball encloses the aqueous humor-filled anterior and posterior chambers of the eye as well as the vitreous body (corpus vitreum). In certain surgical interventions on the eye, it is necessary to remove the vitreous body material from the eyeball. Attempts were being made in this direction as early as the 18th century.

However, vitrectomy did not become a recognized technique until the early nineteen seventies, in particular through the works of Machemer (cf., for example, R. Machemer, Glaskörperchirurgie [Vitreous body surgery], Verlag Hans Huber, Berne, Stuttgart, Vienna, 1981). The works by R. Klöti should also be mentioned (cf. in particular R. Klöti, "Glaskörperverlust—weniger gefährlich mit dem Mikrostripper" [Vitreous body loss—less dangerous with the microstripper], Klin. Mbl. Augenheilkunde (1982); 120: 447–450).

In these early works from the nineteen seventies and nineteen eighties, success was achieved particularly because use was made of motor-driven cutting instruments combined with an aspiration system (Venturi system or peristaltic system). A principal aim of vitrectomy must be to cut through the vitreous body structures and aspirate them in a manner free from forces, since any vitreous body traction entails the risk of rupture of the retina. Conventional aspiration systems are particularly problematic with regard to the vitreous body traction to be avoided, since tensile stresses and shearing stresses cannot always be avoided with these systems. A known mechanical device for vitrectomy has two coaxially guided cannulas, the side wall of the outer cannula being provided with a suction opening for vitreous body material and the inner cannula being axially displaceable with a cutting edge along the opening. Vitreous body material aspirated (suctioned) by underpressure into the cannula is cut by an oscillating movement of the sharp edge of the inner cannula and then suctioned away via the inner cannula.

Another known mechanical vitrectomy system (U.S. Pat. No. 5,487,725 and U.S. Pat. No. 5,547,473) has a rotating cutting head. However, this known technique entails the risk of vitreous body material and even retina in some circumstances winding round the cutting head, which can lead to considerable complications.

Conventional mechanical vitrectomy systems with parts which are moved relative to one another have the disadvantage that the instrument, at the place of insertion into the eye, can only be designed with a substantially straight configuration. This restriction in terms of the shape of the working head of the device means, however, that it is often difficult to reach and remove all areas of the vitreous body from the eyeball. These difficult-to-reach areas (dead spaces) are in particular the base of the vitreous body in the area of the entry opening (that is to say where the cannula is pushed into the eyeball) and opposite the entry opening.

An alternative to the abovementioned mechanical vitrectomy systems is the use of lasers for breaking up the vitreous body substance. Er:YAG laser systems have also been used in this connection. An overview of the prior art is given by Jeffrey W. Berger, Thomas W. Bochow, Jonathan H. Talamo and Donald J. D'Amico in "Measurement and Modeling of Thermal Transients During Er:YAG Laser Irradiation of Vitreous", Lasers in Surgery and Medicine 19; 388–396 (1996).

Er:YAG laser systems have in particular the advantage that at the wavelength of 2.94 mm there is only a small depth of penetration into the vitreous body tissue (approximately 1 to 5 mm). Pulsed laser radiation of this kind also has only a very small zone of damage, both as regards long-term effects and immediate effects.

In the prior art according to DE 38 31 141 A1, mentioned in the introduction, a UV-absorbing substance is given during the microsurgical operation on the eye for the purpose of increasing the rate of ablation.

U.S.Pat. No. 4,122,853 describes microsurgery of the eye with IR radiation, in which the tip of the probe is provided with a special window through which the radiation is deflected into the vitreous body area.

U.S. Pat. No. 4,650,460 describes an electro-pneumatic unit with which it is possible to control the air pressure at which air pulses can be introduced into a pneumatic vitrectomy probe.

German Utility Model G 7439950.1 describes a vitrectomy apparatus with a mechanical rotating comminuting appliance for the vitreous body material. The problems mentioned above in respect of the known mechanical vitrectomy devices can also arise here.

DE 4407949 A1 describes a probe for suctioning off eye tissue with a suction needle which has a needle area, which can be brought into the vicinity of the eye tissue which is to be suctioned, and a lateral opening for a laser beam in this needle area.

In the work by BÜTTNER, H; MACHEMER, R: Erkrankungen am Glaskörper des Auges sind heilbar [Diseases of the vitreous body of the eye are curable] in Umschau, 1974, vol. 74, No. 22, pages 716–717, a vitreous body vitrectomy appliance is described in which an inner tube is rotated in an outer, stationary tube so that, on each rotation, a shearing-off of vitreous body material takes place. This mechanical appliance also has the abovementioned disadvantage that harmful tractions and in particular tensile forces on the vitreous body material can occur.

The invention is based on the object of making available a device of the type mentioned in the introduction, i.e. having an aspiration cannula which has at least one opening through which body substance can be suctioned into the aspiration cannula by means of a suction pump, and having an appliance for detaching and breaking up the body substance in the vicinity of the opening in order to detach aspirated body substance, and with which device it is possible to achieve good operation results free of complications.

According to the invention, this object is achieved by a control system for the appliance for detaching body substance, in particular vitreous body material, and for the suction pump such that the volume of body substance or vitreous body material suctioned through the opening into the aspiration cannula is in each case detached essentially free of traction from the remaining substance, in particular vitreous body material, located in the eye or body before a further volume of substance or vitreous body material is suctioned in. "Free of traction" here signifies that no harmful tractions, in particular tensile forces, occur in the substance or vitreous body material remaining in the body or eye.

In principle, the control, according to the invention, of the aspiration and detachment system can be used on various substances of the human body. The invention is particularly preferably used in vitrectomy. The invention is also well suited to intraocular cataract surgery, i.e. the removal of lens substance.

In principle, the invention can be carried out both with mechanical vitrectomy systems (i.e. with a mechanical cutting appliance) and also with laser vitrectomy systems. The invention is particularly preferably implemented using a laser, namely in such a way that the appliance for detaching vitreous body material has a radiation conductor which conducts pulsed laser radiation to the vicinity of the opening, and that the control system controls the time sequence, energy and length of the laser pulses and the suction pump.

In a preferred embodiment of the invention, the aspiration of vitreous body material (or of other body substance) into the aspiration cannula takes place in the form of a pulsed suctioning, so that on each suction pulse a predetermined amount of vitreous body material is suctioned into the cannula and the suctioning underpressure in the cannula is then reduced until the next laser shot or until the next activation of the mechanical detaching appliance to such an extent that the vitreous body material which has just been suctioned remains only just in the cannula and does not exit from the opening again, i.e. the pressure difference at the opening is just great enough (but not greater) to keep the vitreous body material, machined by radiation or mechanically, inside the cannula, i.e. to prevent it from emerging from the opening.

In another preferred embodiment of the invention, the control system is designed such that as the frequency of activation of the detaching appliance increases, the respective suctioning underpressure in the aspiration cannula is increased. The effect of this is that the same amount of vitreous body material (or body substance) is always suctioned between two cutting operations.

In a further preferred embodiment of the invention, the direction in which laser beam pulses are emitted from the radiation conductor is transverse to the aspiration direction in which vitreous body material is suctioned through the opening into the aspiration cannula.

Another preferred embodiment of the device according to the invention lies in the fact that the radiation conductor runs along the inner wall of the aspiration cannula.

According to another preferred embodiment of the invention, the aspiration cannula is closed at its distal end, particularly in a convex shape, and the opening lies in a side wall of the aspiration cannula directly distally below the exit opening of the radiation conductor from which the laser radiation is emitted.

According to one variant of the invention, the opening is formed in the axially open distal end of the aspiration cannula, and the direction of emission of the laser radiation has an essential radial component.

A particularly clean separation of the vitreous body material is achieved by the fact that the laser radiation emerging from the radiation conductor is active in an area directly and, in the direction of incidence of the vitreous body material, immediately behind the opening in the aspiration cannula.

The invention permits in particular an almost force-free cutting and removal of the vitreous body material (or of other body substance). According to the invention, this object is achieved in particular by the fact that the system as a whole (that is to say in particular the laser and the aspiration pump) is controlled in such a way that only an aspiration of vitreous body material takes place at first, and this vitreous body material is then separated by the laser. The invention is thus based on the knowledge that there must be exact coordination and synchronization of the pulsed laser radiation and of the aspiration of vitreous body material in order to avoid traction on the vitreous body and the retina. The essentially traction-free removal of vitreous body material (i.e. free of tensile forces and free of shearing forces), which is aimed at according to the invention, demands that throughout the entire vitrectomy procedure no appreciable tensile forces or shearing forces, capable of causing ruptures or other complications, are transmitted to the remaining vitreous body material which is still located in the eyeball and which is to be removed at a later stage. This means that compared to the prior art, only very small "portions" of vitreous body material are in each case drawn in stages into the aspiration cannula through the opening. Once a defined small "portion" of vitreous body material is located in the cannula, to the inside of the opening, the portion of vitreous body material is detached by means of the laser pulses, without traction occurring outside the cannula.

The invention is therefore preferably implemented with the aspiration of the vitreous body material into the cannula taking place in a pulsed manner, i.e. the control system of the device can be set in such a way that the suctioning underpressure in the cannula (compared to the pressure in the vitreous body material in the eye) is intermittently higher and lower so that, depending on the cutting performance of the detaching appliance (for example of the laser radiation), only a defined amount of vitreous body material is at any time suctioned into the cannula, whereupon this portion of vitreous body material is broken up and detached while no further vitreous body material is being suctioned. As the vitreous body material is being broken up and detached, the under-pressure prevailing in the cannula (compared to the pressure in the vitreous body material outside the cannula) is set such that the vitreous body material that has just been suctioned remains only just in the active area of the detaching appliance (e.g. the laser radiation) and does not exit again from the opening of the cannula. In principle, this technique for detaching the vitreous body material can also be applied using a mechanical vitrectomy system of the type mentioned in the introduction, in which case a mechanical cutting or detaching appliance is used instead of laser radiation as detaching appliance. It is preferable, in the case of the mechanical appliance, just as in the case of the laser vitrectomy appliance described above, that no more material is suctioned into the cannula than can be cut off in portions.

Figure 2:
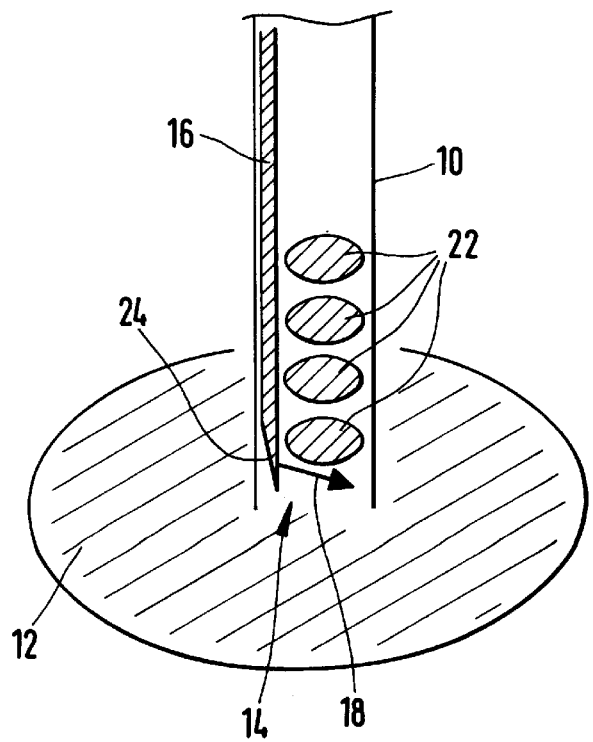

Illustrative embodiments of the invention are explained in greater detail below with reference to the drawing, in which:

FIG. 1 shows, diagrammatically, a first illustrative embodiment of a device for vitrectomy, and FIG. 2 shows a second illustrative embodiment of a device for vitrectomy.

According to FIG. 1, an aspiration cannula 10 is provided which is inserted in a manner known per se into the vitreous body material 12 of an eye. In the figures, the vitreous body material is only indicated diagrammatically. The dimensions, in particular of the cannula, are not true to scale, but have to some extent been enlarged in order to better illustrate the invention.

The aspiration cannula 10 is connected in a manner known per se to a laser radiation source L and to a pump P. By means of the laser radiation source L, laser radiation is coupled in pulsed form into a light conductor 16 which runs inside the aspiration cannula 10. A vacuum is generated in the aspiration cannula by means of the pump P, with which vacuum vitreous body material can be suctioned in, upwards in FIG. 1.

A computer control system C (micro-controller) is provided for controlling, in particular, the parameters of the laser L and the output of the pump P in a manner which will be described in more detail below. The control entails, in particular, also the timed coordination of the laser with respect to the pump, which can be operated in particular periodically (intermittently) and whose aspiration can be adjusted as a function of the laser parameters.

In the illustrative embodiment according to FIG. 1, the distal end 20 of the aspiration cannula 10 is closed. The distal end is convex, in particular semispherical, in order to avoid injuries caused by sharp edges.

Just above the convex distal end 20 of the aspiration cannula, there is an opening 14 in the wall of the cannula, through which opening vitreous body material can be suctioned into the inside of the cannula. Arranged directly adjacent to the opening 14 is the exit opening 26 of the light conductor 16, so that laser radiation 18 emitted through the exit opening 26 is active directly to the inside of the opening 14, i.e. as close as possible to the opening.

The axial direction A and the radial direction R of the system are also indicated in FIG. 1. In this illustrative embodiment, vitreous body material 12 is aspirated in the radial direction R through the opening 14, while the detaching laser beam 18 is oriented in the axial direction A. The direction of the laser beam 18 is thus perpendicular to the aspiration direction of the vitreous body material at the passage through the opening 14. Several "portions" of vitreous body material are successively detached one after the other from the vitreous body material 12 by means of pulsed laser radiation 18 or are liquefied and then, as a result of the pressure drop in the aspiration cannula 10, are suctioned upwards.

The laser L and the pump P are controlled by means of the computer control system C, in terms of the system parameters, in such a way that no volume of vitreous body is suctioned into the cannula if this volume of vitreous body is still so firmly attached to the remaining vitreous body material 12 that there is a risk of generating traction forces on the vitreous body material 12 remaining in the eye.

The suctioning of vitreous body material into the aspiration cannula through the opening 14, and the use of the laser pulses are therefore coordinated and synchronized, in terms of pulse energy, pulse duration and pulse frequency, in such a way that only a relatively small volume of vitreous body material is at any time suctioned through the opening 14, and this relatively small volume is then detached by means of the laser radiation 18 or broken up or liquefied. This avoids suctioning of an excessively large amount of vitreous body material, still connected to the outer vitreous body material 12, as this could lead to the said tractions.

FIG. 2 shows a modified illustrative embodiment in which the opening 14 in the aspiration cannula 10 is designed directly in the distal end of the cannula, and indeed, in the illustrative embodiment according to the figure, essentially across the entire end of the cannula. The exit opening of the light conductor 16 here has a different design from the illustrative embodiment according to FIG. 1. At its end, the light conductor 16 has an oblique mirror surface 24, the effect of which is that radiation 18 emitted from the light conductor 16 runs essentially radially (the terms "radially" and "axially" are explained with reference to FIG. 1). Small "portions" of vitreous body material, suctioned through the opening 14, are successively detached from the remaining vitreous body material 12 by means of the pulsed laser radiation 18. It is not necessary for the detaching to take place in each case with a single laser pulse. A plurality of laser pulses can also be provided in each case to effect the portioning of the vitreous body material, as is indicated by reference number 22 in the figures. Also in the illustrative embodiment according to FIG. 2, the laser radiation is coordinated, in terms of energy, pulse length and pulse repetition frequency, with the suction rate of the pump P, namely in the manner described with reference to FIG. 1.

An Er:YAG solid-state laser is preferably provided as the laser radiation source L. It is also possible to use other laser systems with emission wavelengths which correspond at least to one of the absorption bands of $H_2O$, for example Er,Cr:YAG systems (2.92 $\mu$m wavelength) or Er:YSSG laser systems (wavelength 2.69 $\mu$m).

When using an Er:YAG solid-state laser, the following laser parameters have proven expedient: pulse durations in the range from 50 to 500 $\mu$sec, pulse repetition frequencies of individual pulses of up to 100 Hz, and laser energies in the range from 1 to 100 mJ.

For the light conductor 16, fibre diameters of 50 to 1000 $\mu$m in particular are possible.

The described vitrectomy devices also permit in particular curved structures at the distal end of the aspiration cannula, including the aspiration channel. By this means, the disadvantage of known systems, in particular of mechanical systems, discussed at the beginning, is overcome, namely that certain areas of the eyeball can only be reached with difficulty or at the risk of complications. Every area of the vitreous body can be optimally accessed, and different handpieces can alternatively be arranged in an exchangeable manner at the distal end of the device according to FIGS. 1 and 2.

The portion size of the respective suctioned portions 22 (volumes) of vitreous body material is preferably kept smaller than 0.2 $mm^3$, particularly preferably smaller than 0.1 $mm^3$. In principle, the size of the portions 22 can be kept as small as is necessary. Experimental trials have revealed suitable minimum sizes of portions 22 at 0.0008 $mm^3$.

The diameter of the aspiration cannula 10 is typically 0.5 to 1.5 mm, with good experimental results being obtained with a diameter of 1.3 mm. The diameter of the opening 14 is preferably in the range from 0.1 to 1 mm, with good experimental results being obtained at a diameter of 0.3 mm. In initial trials, a standard suction and irrigation system for vitrectomy was used as suction pump P, with underpressures of 0 to 700 mm Hg for the aspiration.

If a laser is used as the appliance for detaching and breaking up the vitreous body material, and if the laser radiation is guided by means of a radiation conductor 16 in front of the opening 14, it has proven expedient for the portion 22 of vitreous body material, suctioned in on each pulse, to be dimensioned not greater than the area of influence of the laser radiation 18. If the laser radiation 18 has an area of influence with approximately the dimensions of the radiation conductor 16, the consequence of this is that the individual portion 22 has a dimension, in the suction direction (radially in FIG. 1; axially in FIG. 2), which corresponds approximately to the diameter of the radiation conductor 16 (e.g. an optical fibre) or is smaller than this diameter.

Using the parameters specified above, individual pulses, for controlled cutting in zones especially at risk, up to repetition rates of 100 Hz and more have proven expedient for the rapid removal of vitreous body material in less critical zones.

The described laser vitrectomy system permits multiple use, particularly since mechanical wear is avoided, and, as a result of this, the operation costs can be significantly reduced.

We claim:

1. A surgical instrument for the removal of vitreous body material of the eye, the surgical instrument comprising:
   an aspiration cannula having at least one opening through which vitreous body material can be suctioned into the inside of the cannula;
   a laser radiation source connected to the aspiration cannula for providing pulsed laser radiation to sever the vitreous body material;
   a light conductor which runs lengthwise inside of the cannula for conducting the pulsed laser radiation and emitting the pulsed laser radition to the vicinity of the exit opening;
   a pump for generating a vacuum in the aspiration cannula for suctioning vitreous body material and removing severed vitreous body material;
   a computer control system for controlling and synchronizing the pulse parameters of the laser radiation source and the output of the pump, such that the volume of body substance suctioned through the opening into the aspiration cannula is in each case detached essentially free of traction and tensile forces from the remaining body material located in the body before a further volume of body material is suctioned in.

2. Surgical instrument according to claim 1, characterized in that the computer control system controls the time sequence, energy and length of the laser pulses and the suction pump.

3. Surgical instrument according to claim 1, characterized in that the computer control system is designed such that as the frequency of activation of the severing laser radiation pulses is increased and the respective suctioning underpressure in the aspiration cannula is increased such that the same defined amount of the vitreous body material is always suctioned into the aspiration cannula between two severing operations.

4. Surgical instrument according to claim 1, characterized in that the direction in which the pulsed laser radiation are emitted from the light conductor is transverse to the aspiration direction in which vitreous body material is suctioned through the opening into the aspiration cannula.

5. Surgical instrument according to claim 1, characterized in that the aspiration cannula is closed at its distal end and in that the opening lies in a side wall of the aspiration cannula directly distally below the exit opening of the light conductor from which the laser radiation is emitted.

6. Surgical instrument according to claim 5, characterized in that the aspiration cannula is closed at its distal end in a convex shape.

7. Surgical instrument according to claim 1, characterized in that the opening is formed in the axially open distal end of the aspiration cannula and in that the laser radiation has an essential radial component.

8. Surgical instrument according to claim 1, characterized in that the laser radiation emerging from the light conductor is active in an area directly and, in the direction of incidence, immediately behind the opening of the aspiration cannula.

9. A method of removing vitreous body material of the eye by means of:
   an aspiration cannula having at least one opening through which vitreous body material can be suctioned into the inside of the cannula;
   a laser radiation source connected to the aspiration cannula for providing pulsed laser radiation to sever the vitreous body material;
   a light conductor which runs lengthwise inside of the cannula for conducting the pulsed laser radiation and emitting the pulsed laser radiation to the vicinity of the exit opening;
   a pump for generating a vacuum in the aspiration cannula for suctioning vitreous body material and removing severed vitreous body material;
   said method being characterized in that the pulsed parameters of the laser radiation source and the output of the pump are controlled such that the volume of body substance suctioned through the opening into the aspiration cannula is in each case detached essentially free of traction and tensile forces from the remaining body material located in the body before a further volume of body material is suctioned in.

10. A method according to claim 9, characterized in that the time sequence, energy and length of the laser pulses and the suction pump are controlled.

11. A method according to claim 9, characterized in that the frequency of activation of the severing laser radiation pulses is increased and the respective suctioning underpressure in the aspiration cannula is increased such that the same defined amount of the vitreous body material is always suctioned into the aspiration cannula between two severing operations.

* * * * *

UNITED STATES PATENT AND TRADEMARK OFFICE
CERTIFICATE OF CORRECTION

PATENT NO : 6,027,493
DATED : February 22, 2000
INVENTOR(S) : Christof Donitzky; Max Reindl; Fredy Strohm It is certified that error appears in the above-identified patent and that said Letters Patent are hereby corrected as shown below:

Title page, item [56], under "Other Publications," line 9, please delete "Auge4s" and insert in lieu thereof --Auges--.

In column 7, line 16, please delete "radition" and insert in lieu thereof --radiation--.

Signed and Sealed this

Third Day of April, 2001

Attest:

NICHOLAS P. GODICI

Attesting Officer

Acting Director of the United States Patent and Trademark Office